United States Patent [19]

Cherpeck

[11] 4,407,806

[45] Oct. 4, 1983

[54] FUNGICIDAL, HERBICIDAL AND PLANT GROWTH REGULATING PYRIDYL-CONTAINING ETHERS

[75] Inventor: Richard E. Cherpeck, San Rafael, Calif.

[73] Assignee: Chevron Research Company, San Francisco, Calif.

[21] Appl. No.: 323,832

[22] Filed: Nov. 23, 1981

[51] Int. Cl.$^3$ .................... A61K 31/44; C07D 213/16
[52] U.S. Cl. .................................. 424/263; 546/343; 546/339; 71/94
[58] Field of Search .................... 546/339, 343; 71/94; 424/263

[56] References Cited

U.S. PATENT DOCUMENTS

| | | | |
|---|---|---|---|
| 3,396,224 | 8/1968 | Van Heyningen | 424/263 |
| 3,849,423 | 11/1974 | Krumkalns | 546/343 |
| 4,262,000 | 4/1981 | Holmwood et al. | 424/263 |

FOREIGN PATENT DOCUMENTS

| | | | |
|---|---|---|---|
| 45-12319 | 5/1970 | Japan | 546/339 |
| 1595261 | 8/1981 | United Kingdom . | |

*Primary Examiner*—Jane T. Fan
*Attorney, Agent, or Firm*—D. A. Newell; T. G. De Jonghe; L. S. Squires

[57] ABSTRACT

3-Pyridyl ethers of this invention possess good fungicidal, herbicidal and plantgrowth regulating activity.

16 Claims, No Drawings

FUNGICIDAL, HERBICIDAL AND PLANT GROWTH REGULATING PYRIDYL-CONTAINING ETHERS

BACKGROUND OF THE INVENTION

This invention relates to novel 3-pyridyl-containing ethers useful as systemic fungicides, herbicides and plant-growth regulators.

Davenport et al, U.K. Pat. No. 1,218,623, has disclosed substituted 5-pyrimidine compounds which possessed non-systemic fungicidal, herbicidal and plant-growth regulating activity. Belgium Pat. No. 729,996 discloses pyrazinyl compounds possessing fungicidal activity.

Godefrol et al in U.S. Pat. Nos. 3,658,813 and 3,839,574 have disclosed 1-(beta-aryl)ethyl imidazolo ethers and amines as useful fungicides and bacteriocides.

SUMMARY OF THE INVENTION

The 3-pyridyl compounds of this invention are represented by the formula

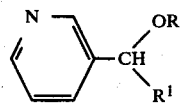 I wherein R is aryl of 6 to 10 carbon atoms; aryl of 6 to 10 carbon atoms substituted with 1 to 3 of the same or different substituents selected from fluoro, chloro, bromo, iodo, nitro, lower alkoxy, lower alkyl or lower alkyl substituted with 1 to 5 of the same or different halogens; arylalkyl of 7 to 12 carbons; arylalkyl of 7 to 12 carbons substituted on the aryl ring with 1 to 3 of the same or different substituents selected from fluoro, chloro, bromo, iodo, nitro, lower alkoxy, lower alkyl or lower alkyl substituted with 1 to 5 of the same or different halogens; biphenyl; biphenyl substituted with 1 to 6 of the same or different substituents selected from fluoro, chloro, bromo, iodo, nitro, lower alkoxy, lower alkyl or lower alkyl substituted with 1 to 5 of the same or different halogens; biphenylalkyl of 13 to 18 carbons; biphenylalkyl of 13 to 18 carbons substituted in the biphenyl rings with 1 to 5 of the same or different substituents selected from fluoro, chloro, bromo, iodo, nitro, lower alkoxy, lower alkyl, or lower alkyl substituted with 1 to 5 of the same or different halogens; or $CH_2R^2$ wherein $R^2$ is lower alkenyl; lower alkenyl substituted with lower alkoxy or with 1 to 5 of the same or different halogens; lower alkynyl; lower alkynyl substituted with lower alkoxy or with 1 to 5 of the same or different halogens; $R^1$ is aryl of 6 to 10 carbons; aryl of 6 to 10 carbons substituted with 1 to 3 of the same or different substituents selected from fluoro, chloro, bromo, iodo, nitro, lower alkyl, lower alkoxy or lower alkyl substituted with 1 to 5 of the same or different halogens; biphenyl; or biphenyl substituted with 1 to 6 of the same or different substituents selected from fluoro, chloro, bromo, iodo, nitro, lower alkoxy, lower alkyl or lower alkyl substituted with 1 to 5 of the same or different halogens.

Among other factors, the present invention is based on my finding that the 3-pyridylphenyl carbinol ethers of this invention are surprisingly effective as systemic fungicides, herbicides and plant growth regulators. In particular, the compounds of this invention show especially effective fungicidal activity against Bean Powdery Mildew. Moreover, some of the compounds are surprisingly effective as plant-growth-regulators. In particular, they prevent lodging in wheat and barley and other grasses by stunting plant height.

The preferred R groups are lower alkenyl, lower alkenyl substituted with 1 to 3 halogens, benzyl and substituted benzyl. Particularly preferred alkenyl R groups are the allyl and 2-chloroallyl groups. Preferred substituted benzyl groups include the 3-trifluoromethylbenzyl, the 4t-butylbenzyl, and the 2,4-dichlorobenzyl.

The preferred $R^1$ groups are phenyl and substituted phenyl. Preferably $R^1$ is phenyl substituted with 1 to 3 of the same or different halogens. Most preferably $R^1$ is 2,4-dihalophenyl.

Representative compounds of this invention include:
3-pyridyl-2,4-dichlorophenylcarbinol allylether;
3-pyridyl-2,4-dichlorophenylcarbinol 2-chloroallylether;
3-pyridyl-2,4-dichlorophenylcarbinol 2,4-dichlorobenzylether;
3-pyridyl-4-methoxyphenylcarbinol 2,4-dichlorobenzylether;
3-pyridyl-2,4-dichlorophenylcarbinol 2,4-dichlorophenylether;
3-pyridyl-4-methoxyphenylcarbinol 2,4-dichlorophenylether;
3-pyridyl-2,4-dichlorophenylcarbinol 3-trifluoromethylbenzylether;
3-pyridyl-2,4-dichlorophenylcarbinol 3-trifluoromethylphenylether;
3-pyridyl-1-naphthylcarbinol allylether;
3-pyridyl-1-naphthylcarbinol 2-chloroallylether;
3-pyridyl-1-naphthylcarbinol 2,4-dichlorophenylether;
3-pyridyl-1-naphthylcarbinol 2,4-dichlorobenzylcarbinol;
3-pyridyl-1-naphthylcarbinol 4-methoxyphenylether;
3-pyridyl-1-naphthylcarbinol 4-trifluoromethylphenylether;
3-pyridyl-1-(4-methylnaphthyl)carbinol 2-chloroallylether;
3-pyridyl-1-(4-methylnaphthyl)carbinol 2,4-dichlorophenylcarbinol;
3-pyridyl-1-(4-methylnaphthyl)carbinol 2,4-dichlorobenzylcarbinol;
3-pyridyl-2,4-dichlorophenylcarbinol 4-t-butylbenzylether;
3-pyridyl-2,4-dichlorophenylcarbinol 4-t-butylphenylether;
3-pyridyl-2,4-dichlorophenylcarbinol 4-nitrophenylether;
3-pyridyl-2,4-dichlorophenylcarbinol propargylether;
3-pyridyl-2,4-dichlorophenylcarbinol but-2-ynylether;
3-pyridyl-2,4-dibromophenylcarbinol allylether;
3-pyridyl-2,4-difluorophenylcarbinol allylether;
3-pyridyl-2,4-diiodophenylcarbinol allylether;
3-pyridyl-2,4-dichlorophenylcarbinol 2-methoxyallylether;
3-pyridyl-4-nitrophenylcarbinol allylether;
3-pyridyl-4-ethoxyphenylcarbinol allylether;
3-pyridyl-4-ethylphenylcarbinol allylether;
3-pyridyl-4-chlorophenylcarbinol allylether;
3-pyridyl-2-chlorophenylcarbinol allylether;
3-pyridyl-4-methoxyphenylcarbinol allylether;

3-pyridyl-2,4-dichlorophenylcarbinol 4-phenylbenzylether;
3-pyridyl-2,4-dichlorophenylcarbinol 3-phenylbenzylether;
3-pyridyl-4-t-butylphenylcarbinol allylether;
3-pyridyl-4-t-butylphenylcarbinol 3-trifluoromethylbenzylether;
3-pyridyl-(4-biphenyl)carbinol allylether;
3pyridyl-(3-biphenyl)carbinol allylether;
3-pyridyl-(2-biphenyl)carbinol allylether;
3-pyridyl-(4-biphenyl)carbinol 2,4-dichlorobenzylether;
3-pyridyl-(3-biphenyl)carbinol 2,4-dichlorobenzylether;
3-pyridyl-(2-biphenyl)carbinol 2,4-dichlorobenzylether;
3-pyridyl-(4-biphenyl)carbinol 4-t-butylbenzylether;
3-pyridyl-(3-biphenyl)carbinol 4-t-butylbenzylether;
3-pyridyl-(2-biphenyl)carbinol 4-t-butylbenzylether;
3-pyridyl-(4-biphenyl)carbinol 2-chloroallylether;
3-pyridyl-(3-biphenyl)carbinol 2-chloroallylether;
3-pyridyl-(2-biphenyl)carbinol 2-chloroallylether;
3-pyridyl-(4-biphenyl)carbinol 3-trifluoromethylbenzylether;
3-pyridyl-(3-biphenyl)carbinol 3-trifluoromethylbenzylether;
3-pyridyl-(2-biphenyl)carbinol 3-trifluoromethylbenzylether;
3-pyridyl-(4-biphenyl)carbinol phenylether;
3-pyridyl-(3-biphenyl)carbinol phenylether;
3-pyridyl-(2-biphenyl)carbinol phenylether;
3-pyridyl-(4-biphenyl)carbinol 2,4-dichlorophenylether;
3-pyridyl-(3-biphenyl)carbinol 2,4-dichlorophenylether;
3-pyridyl-(2-biphenyl)carbinol 2,4-dichlorophenylether;
3-pyridyl-[4-(2',4'-dichlorobiphenyl)]carbinol phenylether;
3-pyridyl-[3-(2',4'-dichlorobiphenyl)]carbinol phenylether;
3-pyridyl-[2-(2',4'-dichlorobiphenyl)]carbinol phenylether.

DEFINITIONS

As used herein the following terms have the following meanings, unless expressly stated to the contrary.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl and the like.

The term "alkenyl" refers to unsaturated alkyl groups having a double bond (e.g., $CH_3CH=CH(CH_2)_2-$, ) and includes both straight- and branched-chain alkenyl groups.

"Lower alkenyl" groups refer to alkenyl groups having from 2 through 6 carbon atoms. Typical lower alkenyl groups include, for example, ethylene; but-3-enyl; hex-4-enyl; 2-methylpent-4-enyl and the like.

The term "alkynyl" refers to unsaturated alkyl groups having a triple bond (e.g. $CH_3C\equiv C(CH_2)_2-$) and includes both straight- and branched-chain alkynyl groups.

The term "lower alkynyl" refers to alkynyl groups having from 2 through 6 carbon atoms and includes, for example, but-3-ynyl; hex-4-ynyl; 3-methylpent-4-ynyl and the like.

The term "halo or halogen atom" refers to the groups fluoro, chloro, bromo and iodo.

The term "alkoxy" refers to the group $R^7O-$ wherein $R^7$ is alkyl.

The term "lower alkoxy" refers to alkoxy groups having from 1 through 6 carbon atoms and includes, for example, methoxy, ethoxy, t-butoxy, hexoxy and the like.

The term "aryl" refers to aryl groups having from 6 through 10 carbon atoms and includes, for example, phenyl, naphthyl, etc.

The term "arylalkyl" refers to an alkyl group of 1 to 4 carbons substituted with an aryl group of 6 to 10 carbons and includes, for example, benzyl, naphthylethyl, 2-phenylpropyl, etc.

The terms "substituted aryl" and "substituted arylalkyl" refer to the radicals which are substituted on the aromatic ring with 1 to 3 of the same or different substituents selected from chloro, fluoro, bromo, iodo, nitro, lower alkoxy, lower alkyl or lower alkyl substituted with 1 to 5 of the same or different halogens. The terms "lower alkyl", "lower alkoxy" and "halogen" have the meanings as defined above.

The term "biphenyl" refers to the group:

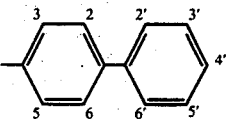

with the conventional numbering system employed. The term "4-biphenyl" indicates substitution at the 4-position while 2-biphenyl indicates substitution at the 2-position

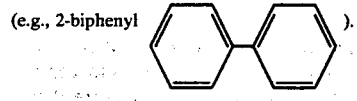

The term "substituted biphenyl" refers to the biphenyl group substituted on either or both aromatic rings with 1 to 6 of the same or different substituents selected from fluoro, chloro, bromo, iodo, nitro, lower alkoxy, lower alkyl or lower alkyl substituted with 1 to 5 of the same or different halogens. The terms "lower alkyl," "lower alkoxy" and "halogen" have the meanings as defined above. Representative examples include for instance 4-[2',4'-dichlorobiphenyl]

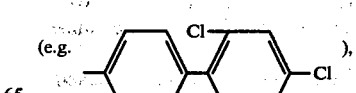

4-[2,6-dimethyl-4'-methoxybiphenyl]

-continued (e.g. 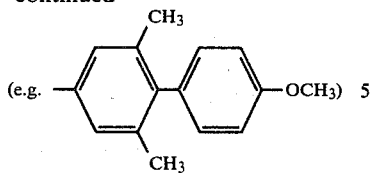)

and the like.

The term "biphenylalkyl" refers to an alkyl group of 1 to 6 carbons substituted with a biphenyl group and includes, for example, 4-biphenylmethyl (e.g. 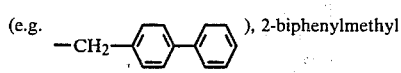), 2-biphenylmethyl (e.g. 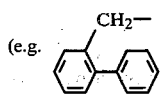), 4-biphenylisopropyl (e.g. 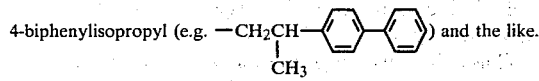) and the like.

The term "substituted biphenylalkyl" refers to the biphenylalkyl group substituted on either or both aromatic rings with 1 to 5 of the same or different substituents selected from chloro, fluoro, bromo, iodo, nitro, lower alkoxy, lower alkyl or lower alkyl substituted with 1 to 5 of the same or different halogens. The terms "lower alkyl", "lower alkoxy" and "halogen" have the meanings as defined above.

DETAILED DESCRIPTION OF THE INVENTION

The compounds of this invention are prepared according to the synthetic scheme shown below:

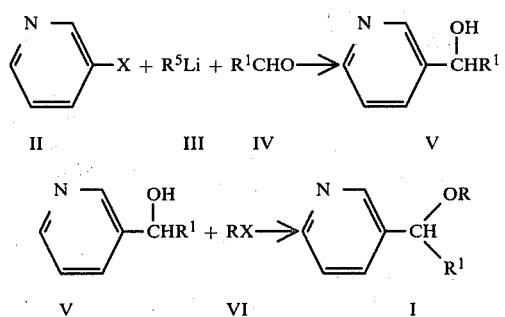

where X is halogen and R, and $R^1$ are as defined above and $R^5$ is lower alkyl.

Reaction 1 is conducted by adding an alkyllithium (III), in hexane, to an inert anhydrous organic solvent such as diethylether, tetrahydrofuran, hexane and the like. Preferably, butyllithium, a 1.6 molar solution in hexane, is used in reaction 1. The reaction is conducted at atmospheric pressure under an inert atmosphere such as nitrogen, argon and the like. After addition, the system is cooled to between −50° C. and −150° C. Preferably, the temperature is maintained at from −100° C. to −130° C. An essentially equimolar amount of II is then added to the system and the system is stirred for ¼ to 10 hours. Afterwards, an essentially equimolar amount of IV is added while maintaining the system at the same constant temperature (±20° C.). After addition of IV, the system is maintained at the same constant temperature (±20° C.) for from 1 to 5 hours and then allowed to come to room temperature over a period of from 2 to 12 hours. The system is quenched with saturated aqueous ammonium chloride. The product, V, is then isolated by conventional procedures such as extraction, filtration, chromtography, distillation or alternatively is used directly in reaction 2 without purification and/or isolation.

Reaction 2 is conducted by adding the alcohol, V, to an inert anhydrous organic solvent such as diethylether, benzene, toluene, tetrahydrofuran, hexane, dimethyl formamide and the like. The solvent of choice for reaction 2 is tetrahydrofuran. The reaction is conducted at atmospheric pressure under an inert atmosphere such as argon, nitrogen and the like. After addition of V, the system is cooled to between −78° C. to room temperature, although preferably, the temperature is maintained at between −10° C. and 10° C. An essentially equimolar amount of a strong base such as sodium hydride and the like is then added to the system. The system is then treated with an essentially equimolar amount of VI while still at the same constant temperature (±10° C.). After addition of VI, the system is allowed to come to room temperature over a period of from 1 to 6 hours. After reaching room temperature, the system is heated at reflux for from 1 to 24 hours. The product, I, is then isolated by conventional procedures such as extraction, filtration, chromatography, distillation and the like.

Alternatively, the 3-pyridylphenylcarbinols of formula V may be prepared by reducing the commercially available ketone, VII, as shown in reaction 3 below:

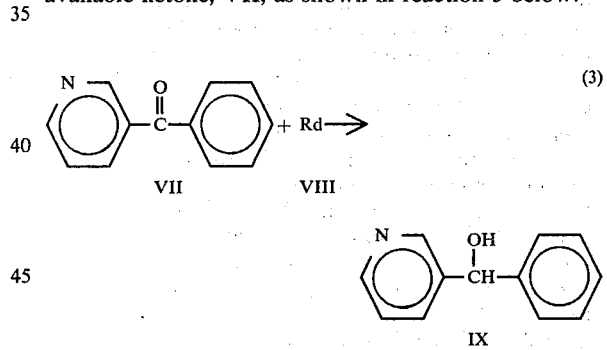

here Rd is a reducing agent. Essentially equimolar amounts of the 3-pyridylphenylketone, VII, and the reducing agent are added together. The reaction is conducted in the liquid phase using an organic solvent such as methanol, ethanol, tetrahydrofuran and the like. Suitable reducing agents, VIII, include sodium borohydride, lithium aluminum hydride and the like while the preferred reducing agent is sodium borohydride. The reaction is conducted at temperatures of from −78° C. to 50° C. although preferably the reaction is done from 0° C. to 10° C. Reaction pressure is not critical and for convenience the reaction is conducted at atmospheric pressure. The reaction is complete in from 1 to 48 hours. The product IX is then isolated by conventional procedures such as extraction, filtration, chromatography, distillation or alternatively is used directly in reaction 2 without purification and/or isolation. Product IX is then converted to the products of formula I by the method described in reaction 2.

Alternatively, in preparing the phenyl and biphenyl ethers of formula I, the preferred method is shown by the following scheme:

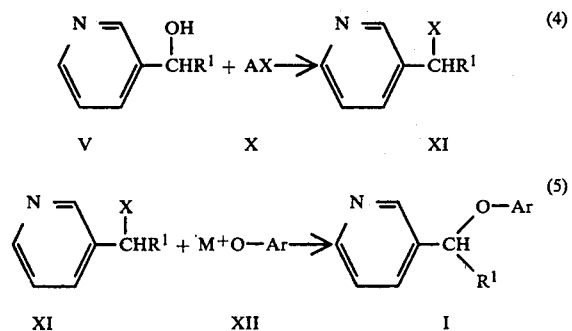

where AX represents a halogenating agent, M represents a monovalent cation, X represents a halogen, and Ar and R¹ are as defined above.

Reaction 4 is conducted by adding V to a solution containing approximately 1.2 equivalents of X. The reaction is done in the liquid phase using an inert organic solvent such as tetrahydrofuran, chloroform, methylenechloride and the like. Alternatively, an excess of the halogenating agent such as thionyl chloride, oxalyl chloride and the like may be used in lieu of a solvent. The preferred halogenating agent is thionyl chloride. The reaction is conducted at temperatures from 0° C. to 100° C. Reaction pressure is not critical and for convenience the reaction is conducted at atmospheric pressure. The reaction is generally complete within 1 to 24 hours. The product, XI, is then isolated by conventional procedures such as extraction, filtration, chromatography, distillation, or alternatively is used directly in reaction 5 without purification and/or isolation.

Reaction 5 is conducted by first preparing the metal salt of phenol or the substituted phenol used. This salt is prepared by adding an essentially equimolar amount of metallic sodium to the phenol. The reaction is done in the liquid phase using an inert organic solvent such as toluene, benzene and the like. The reaction is conducted at temperatures of from 0° C. to 150° C. Reaction pressure is not critical and for convenience the reaction is conducted at atmospheric pressure. After addition of the metallic sodium, an essentially equimolar amount of the halide XI is added. The system is stirred at from 0° C. to 150° C. Reaction pressure is not critical and for convenience the reaction is conducted at atmospheric pressure. The reaction is generally complete within 1 to 72 hours. The product I is then isolated by conventional procedures such as extraction, filtration, chromatography, distillation and the like.

Utility

The compounds of this invention are useful for controlling fungi, particularly plant fungal infections caused by Botrytis cinerea, leaf blights caused by organisms such as *Phytophthora infestans conidia, alternaria solani conidia, septoria apii* and powdery mildew caused by organisms such as *Erisiphe polygoni*.

However, some fungicidal compounds of the invention may be more fungicidally active than others against particular fungi. Tables III and VI list a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, organic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried no relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bacteriocides, plant growth regulators, fertilizers, etc.

Some of the compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds, when applied to growing plants above the ground in which an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, attapulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

For plant growth regulating or retarding activity, it is essential to apply the compounds of the invention at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

A further understanding of the invention can be had on the following non-limiting Examples. Wherein, unless expressly stated to the contrary, all temperatures and temperature ranges refer to the Centigrade system and the term "ambient" or "room temperature" refers to about 20° to 25° C. The term "percent" refers to weight percent and the term "mol" or "mols" refers to gram mols. the term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products.

EXAMPLES

EXAMPLE 1

Preparation of the 3-pyridyl-2,4-dichlorophenylcarbinol

To a 500 ml 3-neck round bottom flask equipped with an addition funnel, septum, thermometer and an argon inlet was added 150 ml of anhydrous diethyl ether and 94 ml of 1.6 molar butyllithium solution (in hexane). The system was cooled to $-120°$ C. and 14.5 ml of 3-bromopyridine in 75 ml of tetrahydrofuran was added over 1 hour. After addition of the 3-bromopyridine, the system was stirred for an additional 45 minutes. At this time, 26.25 gm of 2,4-dichlorobenzaldehyde in 75 ml of tetrahydrofuran was added to the system while still maintaining at temperatures of $-120°$ C. The system was kept at $-120°$ C. for an additional 6 hours after addition of the 2,4-dichlorobenzaldehyde and afterwards allowed to come to room temperature. After 10 hours at room temperature, the system was quenched with saturated ammonium chloride (in water). The system was then adjusted to a pH 2 with concentrated HCl solution. The solution was extracted with diethyl ether. The aqueous solution was made basic with a 50% NaOH solution. The product was extracted with methylene chloride and then dried over sodium sulfate. The methylene chloride was removed by stripping to give 25.75 gm of the 3-pyridyl-2,4-dichlorophenyl-carbinol as tan solid, m.p. 108°–111° C., and listed as compound number 2 in Table I.

EXAMPLE 2

Preparation of the 3-pyridyl-1-naphthylcarbinol

To a 500 ml 3-neck flask round bottom flask equipped with an addition funnel, septum, thermometer and an argon inlet is added 100 ml of anhydrous diethyl ether and 62.5 ml of 1.6 molar butyllithium solution (in hexane). The system is cooled to −120° C. and 15.90 gm of 3-bromopyridine in 50 ml of tetrahydrofuran is added over 2 hours. After addition of the 3-bromopyridine, the system is stirred for an additional 45 minutes. At this time, 15.60 gm of 1-formylnaphthalene in 50 ml of tetrahydrofuran is added to the system while still maintaining a temperature of −120° C. The system is kept at −120° C. for an additional 3 hours after addition of the 1-formylnaphthalene and afterwards is allowed to come to room temperature. After 10 hours at room temperature, the system is quenched with saturated ammonium chloride (in water). The system is adjusted to pH 2 with HCl solution. The solution is extracted with diethyl ether. The aqueous solution is made basic with a 5% NaOH solution. The product is extracted with methylene chloride and dried over sodium sulfate. The methylene chloride is removed by stripping and the residue is triturated with hexane to give the 3-pyridyl-1-naphthylcarbinol.

EXAMPLE 3

Preparation of the 3-pyridylphenylcarbinol 50.0 gms of phenyl-3-pyridyl ketone was added to 650 ml of methanol and the system was then cooled to 0° to 5° C. After cooling, 15.5 gms of sodium borohydride was added in 3 parts. After addition, the system was allowed to come to room temperature. The system was then refluxed for 1 hour and stirred for an additional 72 hours at room temperature. The methanol was removed by stripping. Afterwards, 575 ml of 5% HCl solution was added to the residue and the system refluxed for 15 minutes. The acid was neutralized with 50% NaOH solution and the product extracted with methylene chloride to give the 3-pyridylphenylcarbinol as a white solid, m.p. 53° to 60° C.

EXAMPLE 4

Preparation of the 3-pyridyl-2,4-dichlorophenylcarbinol allylether

To a 250 ml single neck round bottom flask equipped with a reflux condensor and an argon inlet was added 3.56 gm of the 3-pyridyl-2,4-dichlorophenylcarbinol and 60 ml of anhydrous tetrahydrofuran. The system was cooled to 0° C. and after cooling 0.37 gm sodium hydride added. The system was stirred for 75 additional minutes and 1.45 ml of allyl bromide was then added. The system was allowed to come to room temperature over ½-hour and stirred there for an additional 1 hour. Afterwards the system was heated at reflux for 18 hours. At this time, water was added to the system and the product extracted with methylene chloride. The methylene chloride was then washed with water and then dried over sodium sulfate. The methylene chloride was removed by stripping to give 1.73 gm of the 3-pyridyl-2,4-dichlorophenylcarbinol allylether and listed as compound number 3 in Table I.

EXAMPLE 5

Preparation of the 3-pyridyl-phenylcarbinol 4-phenylbenzylether

To a 250 ml single neck round bottom flask equipped with a reflux condensor and an argon inlet was added 3.50 gm of the 3-pyridyl-phenylcarbinol and 60 ml of anhydrous tetrahydrofuran. The system was cooled to 0° C. and after cooling 0.50 gm of sodium hydride was added. The system was allowed to come to room temperature. 4.66 gm of 4-phenylbenzylchloride was added and the system was then refluxed for 18 hours. At this time, water was added to the system and the product was extracted with methylene chloride. The methylene chloride was then washed with water and then dried over sodium sulfate. The methylene chloride was removed by stripping to give the 3-pyridylphenylcarbinol 4-phenylbenzylether, the product was purified by column using chromatography, a silica gel column and eluted with 2:3 ethylacetate:hexane. The solvent was stripped to give 0.7 gm of product, m.p. 78°–81° C. and listed as compound number 11, Table I.

EXAMPLE 6

Preparation of the 3-pyridyl-1-naphthylcarbinol allylether

To a 250 ml single neck round bottom flask equipped with a reflux condensor and an argon inlet is added 2.35 gm of the 3-pyridyl-1-naphthylcarbinol and 100 ml of anhydrous tetrahydrofuran. The system is cooled to 0° C. and after cooling 0.26 gm sodium hydride is added. The system is stirred for an additional 20 minutes and 1.1 ml of allyl bromide is added. The system is allowed to come to room temperature over ½-hour and is stirred there for an additional 2 hours. Afterwards, the system is heated at reflux for 17 hours. At this time, water is added to the system and the product extracted with methylene chloride. The methylene chloride is then washed with water and dried over sodium sulfate. The methylene chloride is removed by stripping to give the 3-pyridyl-1-naphthylcarbinol allylether.

EXAMPLE 7

Preparation of the 3-pyridyl-2,4-dichlorophenylcarbinol phenylether

To a 100 ml Erlenmeyer flask equipped with a reflux condensor is added 2.54 gm of 3-pyridyl-2,4-dichlorophenylcarbinol and 30 ml of chloroform. The system is cooled to 0° C. and 1.31 gm (1.2 equivalents) of thionyl chloride in 25 ml of chloroform is added over ½-hour. After addition of the thionyl chloride, the system is allowed to come to room temperature and stirred there for 2 hours. The system is then heated at reflux for 1 hour. The chloroform is removed by stripping to give the alpha-chloro-alpha-(3-pyridyl)-2,4-dichlorotoluene hydrochloride salt.

The salt is placed in methylene chloride, washed with saturated aqueous sodium bicarbonate, dried over sodium sulfate and stripped to give the alpha-chloro-alpha-(3-pyridyl)-2,4-dichlorotoluene.

1 gm of phenol is added to 100 ml of toluene in a 250 Erlenmeyer flask equipped with a refluxing condensor. 0.26 gm sodium is added and the system is heated at reflux until the sodium has dissolved. The system is then allowed to come to room temperature. At this time, 2.50 gm of alpha-chloro-2,4-dichloro-alpha-(3-pyridyl)toluene in 30 ml of toluene is added over 1 hour. The system is then heated at reflux for 6 hours. The system is added to water and the product extracted in the organic phase. The toluene is removed by stripping to give the 3-pyridyl-2,4-dichlorophenylcarbinol phenylether.

Compounds made in a manner consistent with Examples 1–7 are found in Table I.

EXAMPLE 8

Preparation of the 3-pyridyl-4-methoxyphenylcarbinol

To a 500-ml 3-neck round bottom flask equipped with an addition funnel, septum, thermometer and an argon inlet is added 150 ml of anhydrous diethylether and 94 ml of 1.6 molar butyllithium solution (in hexane). The system is cooled to −120° C. and 23.8 gm of 3-bromopyrimidine in 75 ml of anhydrous tetrahydrofuran is added over 2 hours. After addition of the 3-bromopyridine, the system is stirred for an additional 45 minutes at this time, 18.3 ml of 4-methoxybenzaldehyde in 75 ml of tetrahydrofuran is added to the system while maintaining a temperature of −120° C. The system is kept at −120° C. for an additional 5 hours after addition of the 4-methoxy-benzaldehyde and afterwards the system is allowed to come to room temperature. After 10 hours at room temperature, the system is quenched with saturated ammonium chloride (in water). The system is adjusted to pH 2 with concentrated HCl solution. The solution is extracted with ether. The aqueous solution is then made basic with a 50% NaOH solution. The product is extracted with methylene chloride which then dried over sodium sulfate. The methylene chloride is removed by stripping and the residue triturated with hexane to give the 3-pyridyl-4-methoxyphenylcarbinol, which is converted to the compounds of this invention as described in Examples 1–7.

EXAMPLE 9

Bean Powdery Mildew

The compounds of the invention were tested for the control of the Bean Powdery Mildew organism *Erisiphe polygoni*. Seedling bean plants were sprayed with a 250 ppm solution of the test compound in acetone, water and a nonionic emulsifier. The sprayed plants were then inoculated 1 day later with organism. The plants were maintained for 10 days at temperatures of 68° F. at night with daytime temperatures of 72° to 80° F.; reative humidity was maintained at 40% to 60%. The percent disease control provided by a given test compound was based on the percent disease reduction relative to the untreated check plants. The results are tabulated in Table II.

EXAMPLE 10

Tomato Early Blight

Compounds of the invention were tested for the control of the tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, placed in the environmental chamber and incubated at 66 to 68% and 100% relative humidity for 24 hours. Following the incubation, the plants were maintained in a greenhouse for about 12 days. Percent diseases control was based on the percent disease development on untreated check plants. The compounds tested and the results are tabulated in Table II.

EXAMPLE 11

Grape Downy Mildew Control

The compounds of the invention were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse seven to nine days; then the amount of disease control was determined. The percent disease control provided by a given test compound was based on the percent disease reduction relative to untreated check plants. The results are tabulated in Table II.

EXAMPLE 12

Tomato Late Blight

Compounds of the invention were tested for the preventative control of the Tomato Late Blight organism *Phytophthora infestans*. Five- to six-weed-old tomato (cultivar Bonny Best) seedlings were used. The tomato plants were sprayed with a 250 ppm suspension of the test compound in acetone, water and a small amount of a nonionic emulsifier. The sprayed plants were then inoculated one day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II. In Table II the test concentration is 250 ppm unless otherwise indicated by the figures in parentheses.

EXAMPLE 13

Celery Late Blight

The celery late blight tests were conducted using celery (Utah) plants 11 weeks old. The celery late blight organism was *Septoria apii*. The celery plants were sprayed with solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table II.

EXAMPLE 14

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of oil and the test solution was sprayed uniformly onto the soil surface at a dose of 33 micrograms/cm². The pot was watered and placed in a greenhouse. The pot was watered intermittently and was observed for seedling emergence, health of emerging seedlings, was observed for seedling emergence, heath of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table III.

EXAMPLE 15

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 micrograms/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table III.

EXAMPLE 16

Axillary Bud Growth Inhibition Of Pinto Bean Plants

Compounds of this invention were tested to determine their plant-growth-retarding effects on axillary bud growth of pinto beans.

Idaho pinto bean plants (13–16 days old) having monofoliate leaves fully developed and first trifoliates beginning to unfold were used. All growth 5 mm above the monofoliate leaf node was removed with forceps 1 to 4 hours prior to treatment with the test compounds. Four plants were used for each test compound.

A 625-ppm solution of the test compound in a 2% aqueous acetone solution containing a small amount of a nonionic surfactant was sprayed onto the pinto bean plants until runoff. After drying, the treated plants were transferred to a greenhouse maintained at 20°–23° C. and watered at regular intervals. Twelve days after treatment, the bud growth at the axil of the monofoliate leaf was determined and expressed as percent inhibition of axillary bud growth as compared to untreated check plants. The percent inhibition for the compounds of this invention is reported in Table IV.

EXAMPLE 17

Cotton Regrowth

Compounds of this invention were tested to determine their plant-growth regulating effects on cotton leaf regrowth.

Cotton plants, 4 to 5 weeks old, containing 4 true leaves above the cotyledonary leaves are employed. Growth beyond the second true leaf was removed. Within 24 hours the plants are sprayed with a 2000 ppm solution of the test compound. After spraying, the plants are transferred to a greenhouse maintained at 85° F. (±5° F.) and incubated there for from 13 to 18 days. The plants during this period are sub-irrigated in ¼" of water.

After this period, regrowth is determined as a percent inhibition of auxiliary bud regrowth—100% is total inhibition while 0% is no inhibition. The results for this test are reported in Table IV.

TABLE I

Compounds of the Formula

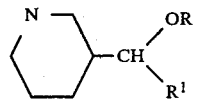

| Compound No. | R | R=CH₂R² R² | R¹ | ANALYSIS Carbon Calc. | Found | Hydrogen Calc. | Found | Nitrogen Calc. | Found | Form |
|---|---|---|---|---|---|---|---|---|---|---|
| 1 | —CH₂-(cyclohexyl with Cl, Cl) | | (cyclohexyl with Cl, Cl) | 55.23 | 52.32 | 3.17 | 3.12 | 3.39 | 2.81 | oil |
| 2 | H | | 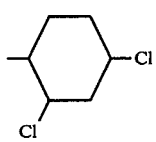 | 56.71 | 57.53 | 3.57 | 3.89 | 5.51 | 5.61 | tan solid |

TABLE I-continued

Compounds of the Formula

![structure: piperidine-N with CH(OR)(R¹) substituent]

| Compound No. | R | R=CH₂R² / R² | R¹ | Carbon Calc. | Carbon Found | Hydrogen Calc. | Hydrogen Found | Nitrogen Calc. | Nitrogen Found | Form |
|---|---|---|---|---|---|---|---|---|---|---|
| 3 |  | —CH=CH₂ | 3,4-dichlorocyclohexyl | 61.24 | 61.34 | 4.45 | 4.96 | 4.76 | 4.68 | oil |
| 4 |  | —C(Cl)=CH₂ | 3,4-dichlorocyclohexyl | 54.81 | 55.33 | 3.68 | 3.95 | 4.26 | 4.30 | oil |
| 5 | —CH₂–(3-CF₃-cyclohexyl) |  | 3,4-dichlorocyclohexyl | 58.27 | 56.85 | 3.42 | 3.54 | 3.40 | 2.97 | oil |
| 6 | —CH₂–(4-C(CH₃)₃-cyclohexyl) |  | 3,4-dichlorocyclohexyl | 69.02 | 68.99 | 5.79 | 6.70 | 3.50 | 3.47 | oil |
| 7 | —CH₂–cyclohexyl |  | cyclohexyl | 82.87 | 82.03 | 6.23 | 6.34 | 5.09 | 5.78 | liquid |
| 8 | —CH₂–(3-CF₃-cyclohexyl) |  | cyclohexyl |  | 67.69 | 4.70 | 4.93 |  | 4.54 | oil |
| 9 |  | —CH=CH₂ | cyclohexyl | 79.97 | 82.04 | 6.71 | 7.16 | 6.22 | 6.73 | oil |
| 10 | —CH₂–(3,4-dichlorocyclohexyl) |  | cyclohexyl | 66.29 | 67.12 | 4.39 | 4.79 | 4.07 | 4.48 | yellow solid |
| 11 | —CH₂–bicyclohexyl |  | cyclohexyl | 85.44 | 83.30 | 6.02 | 5.98 | 3.99 | 3.90 | beige solid |

TABLE II

| Compound Number | Grape D.M. | Fungicidal Activity Control % | | | |
|---|---|---|---|---|---|
| | | Tomato L.B. | Celery L.B. | Tomato E.B. | Bean P.M. |
| 1 | 0 | 4 | 88 | — | 100 |
| 2 | 25 | 0 | 31 | — | 100 |
| 3 | 15 | 0 | 48 | 4 | 100 |
| 4 | 27 | 0 | 83 | 73 | 100 |
| 5 | 12 | 0 | 91 | 71 | 100 |
| 6 | 50 | 0 | 78 | 40 | 100 |
| 7 | 0 | 0 | 43 | 0 | 100 |
| 8 | 0 | 0 | 38 | 25 | 100 |
| 9 | 21 | 0 | 0 | 25 | 0 |
| 10 | 0 | 0 | 64 | 70 | 100 |
| 11 | 13 | 0 | 47 | 5 | 100 |

Grape D.M. — Grape Downy Mildew
Tomato L.B. — Tomato Late Blight
Celery L.B. — Celery Late Blight
Tomato E.B. — Tomato Early Blight
Bean P.M. — Bean Powdery Mildew

TABLE III

| Compound Number | Herbicidal Activity Pre-Emergence/Post-Emergence[1] % Control | | | | | | |
|---|---|---|---|---|---|---|---|
| | L'Qtr. | Mustard | Pigweed | Crab Grass | Water Grass | Wild Oats | Soybean |
| 1 | 0/20 | 0/30 | 0/30 | — | — | — | 0/20 |
| 2 | — | — | — | — | — | — | — |
| 3 | 98/60 | 45/25 | 85/50 | 90/0 | 73/0 | — | 0/33 |
| 4 | 73/55 | 30/58 | 35/45 | 70/0 | 83/0 | 33/0 | 0/28 |
| 5 | 25/63 | 25/40 | 45/55 | 70/0 | 55/0 | 15/0 | 30/30 |
| 6 | 15/60 | 20/25 | 35/55 | 68/0 | 65/0 | 25/0 | 0/35 |
| 7 | 28/65 | 0/60 | 32/45 | 99/0 | 80/0 | — | 0/35 |
| 8 | 0/40 | 0/50 | 0/50 | — | — | — | 0/25 |
| 9 | — | — | — | — | — | — | — |
| 10 | 15/70 | 0/65 | 0/60 | 58/0 | 75/0 | — | 0/50 |

L'Qtr — Lambsquarter (*Chenopodium album*)
Mustard — *Brassica arvensis*
Pigweed — *Amaranthus retraflexus*
Crabgrass — *Digitaria sanguinalis*
Watergrass — *Echinochloa crusgalli*
Wild Oats — *Avena fatura*
Soybean —
— = 0/0

TABLE IV

| Compound # | Plant Growth Regulators | | |
|---|---|---|---|
| | Bud Inhib | Regrowth | Other |
| 1 | 85 | 55 | A |
| 2 | 0 | 0 | — |
| 3 | 25 | 0 | B |
| 4 | 30 | 0 | B |
| 5 | 70 | 65 | C,D |
| 6 | 60 | 90 | C,D |
| 7 | 20 | 90 | G |
| 8 | 60 | 65 | E,F |
| 9 | 25 | 0 | F |
| 10 | 45 | 80 | A |
| 11 | 0 | — | — |

A. New Growth deformed in Bud inhibition
B. Secondary growth deformed in Bud inhibition
C. Bean Trifoliates deformed
D. Pigweed deformed
E. Regrowth deformed
F. Trifoliates deformed in Bud inhibition
G. Tips of new leaves deformed
Bud Inhib = Auxiliary Bud-Growth Inhibition
Regrowth = Cotton Regrowth

What is claimed is:

1. A compound having the formula:

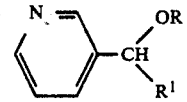

wherein
R is benzyl; benzyl substituted on the phenyl ring with 1 to 5 of the same of different substituents selected from fluoro, chloro, bromo, iodo, nitro, lower alkoxy, lower alkyl or lower alkyl substituted with 1 to 5 of the same or different halogen; or —$CH_2R^2$ wherein $R^2$ is lower alkenyl or lower alkenyl substituted with lower alkoxy or with 1 to 5 of the same or different halogens; and
$R^1$ is phenyl or phenyl substituted with 1 to 5 of the same or different substituents selected from fluoro, chloro, bromo, iodo, nitro, lower alkoxy, lower alkyl or lower alkyl substituted with 1 to 5 of the same or different halogens.

2. A compound of the formula described in claim 1 wherein R is benzyl or benzyl substituted on the aromatic ring with 1 to 5 of the same or different substituents selected from fluoro, chloro, bromo, iodo, nitro, lower alkoxy, lower alkyl or lower alkyl substituted with 1 to 5 of the same or different halogens.

3. A compound of the formula described in claim 1 wherein $R^2$ is lower alkenyl or lower alkenyl substituted with lower alkoxy or with 1 to 5 of the same or different halogens.

4. A compound of the formula described in claim 1 wherein $R^1$ is 2,4-dichlorophenyl.

5. A compound of the formula described in claim 4 wherein R is 2,4-dichlorobenzyl.

6. A compound of the formula described in claim 4 wherein R is 3-trifluoromethylbenzyl.

7. A compound of the formula described in claim 4 wherein R is 4-t-butylbenzyl.

8. A fungicidal composition comprising a biologically inert carrier and a fungicidally effective amount of the compound defined in claim 1.

9. A herbicidal composition comprising a herbicidally effective amount of a compound defined in claim 1 and a biologically inert carrier with the proviso that when $R^1$ is phenyl, R is not allyl.

10. A plant-growth-regulating composition comprising a biologically inert carrier and a plant-growth-regulating amount of the compound of the formula defined in claim 1.

11. A plant-growth-regulating composition comprising a biologically inert carrier and a plant-growth-regulating amount of the compound of the formula defined in claim 1.

12. A method for the control of fungi which comprises contacting said fungi or their growth environment with a fungicidally effective amount of the formula defined in claim 1.

13. A method according to claim 12 where the fungus is Bean Powdery Mildew.

14. A method for controlling undesirable vegetation which comprises applying to said vegetation or its growth medium a herbicidally effective amount of a compound defined in claim 1 with the proviso that when $R^1$ is phenyl, R is not allyl.

15. A method for regulating plant growth which comprises applying to said plants or their growth environment an amount of the compound of the formula defined in claim 1 effective to retard plant growth.

16. A method for regulating plant growth which comprises applying to said plants or their growth environment an amount of the compound of the formula defined in claim 1 effective to retard plant growth.

* * * * *

UNITED STATES PATENT AND TRADEMARK OFFICE
// ## CERTIFICATE OF CORRECTION

PATENT NO. : 4,407,806

DATED : October 4, 1983

INVENTOR(S) : Richard E. Cherpeck

Page 1 of 2

It is certified that error appears in the above-identified patent and that said Letters Patent are hereby corrected as shown below:

Cols. 15 and 16

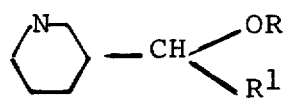   should be   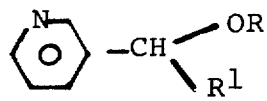

In compounds Nos. 1 and 2

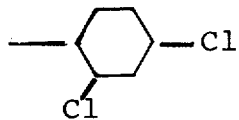   should be   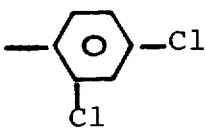

Cols. 17 and 18  TABLE I continued

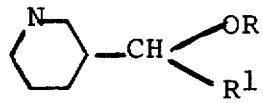   should be   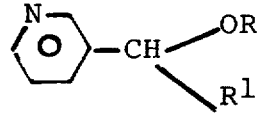

In compounds Nos. 3-11 - Each substituent shown as a cyclohexyl or substituted cyclohexyl ring should be shown

UNITED STATES PATENT AND TRADEMARK OFFICE
CERTIFICATE OF CORRECTION

PATENT NO. : 4,407,806
DATED : October 4, 1983
INVENTOR(S) : Richard E. Cherpeck It is certified that error appears in the above-identified patent and that said Letters Patent is hereby corrected as shown below:

as phenyl or substituted phenyl respectively.

Signed and Sealed this

Twenty-fourth Day of April 1984

[SEAL]

Attest:

GERALD J. MOSSINGHOFF

Attesting Officer

Commissioner of Patents and Trademarks